United States Patent [19]

White

[11] Patent Number: 5,156,641
[45] Date of Patent: Oct. 20, 1992

[54] NASO-GASTRIC CATHETER ANCHOR SYSTEM

[75] Inventor: Kenneth S. White, Rochester, Minn.

[73] Assignee: Mayo Foundation for Medical Education and Research, Rochester, Minn.

[21] Appl. No.: 489,918

[22] Filed: Mar. 7, 1990

[51] Int. Cl.$^5$ .................. A61M 15/08; A61M 5/32; A62B 7/00

[52] U.S. Cl. .................. 128/207.18; 128/DIG. 26; 604/180

[58] Field of Search .................. 128/207.17, DIG. 26, 128/207.18, 911, 912, 200.26, 204.18; 604/174, 177, 178, 179, 180

[56] References Cited

U.S. PATENT DOCUMENTS

| | | | |
|---|---|---|---|
| 3,114,373 | 12/1963 | Andersen | 604/45 |
| 3,146,778 | 9/1964 | Krawiec | 128/DIG. 26 |
| 3,176,690 | 4/1965 | H'Doubler | 128/DIG. 26 |
| 3,288,136 | 11/1966 | Lund | 604/180 |
| 3,288,137 | 11/1966 | Lund | 604/180 |
| 3,777,761 | 12/1973 | Sheridan | 128/DIG. 26 |
| 3,782,388 | 1/1974 | Page | 128/DIG. 26 |
| 3,977,407 | 8/1976 | Coleman et al. | 128/DIG. 26 |
| 4,057,066 | 11/1977 | Taylor | 128/DIG. 26 |
| 4,120,304 | 10/1978 | Moor | 128/DIG. 26 |
| 4,156,428 | 5/1979 | Henkin | 128/207.15 |
| 4,248,229 | 2/1981 | Miller | 128/DIG. 26 |
| 4,326,515 | 4/1982 | Shaffer et al. | 128/DIG. 26 |
| 4,331,143 | 5/1982 | Foster | 128/207.17 |
| 4,527,559 | 7/1985 | Roxburg et al. | 128/DIG. 26 |
| 4,592,351 | 6/1986 | Smith et al. | 128/207.18 |
| 4,641,646 | 2/1987 | Schultz et al. | 128/DIG. 26 |
| 4,774,943 | 10/1988 | Yu | 128/DIG. 26 |
| 4,823,789 | 4/1989 | Beisang, III | 128/DIG. 26 |
| 4,838,878 | 6/1989 | Kalt et al. | 128/DIG. 26 |
| 4,844,061 | 7/1989 | Carroll | 128/207.17 |
| 4,932,943 | 6/1990 | Nowak | 128/DIG. 26 |
| 4,955,864 | 9/1990 | Hajduch | 604/174 |
| 4,995,384 | 2/1991 | Keeling | 128/204.18 |

FOREIGN PATENT DOCUMENTS 0234746 9/1987 United Kingdom ........... 128/200.24

Primary Examiner—Edgar S. Burr
Assistant Examiner—Kimberly L. Asher
Attorney, Agent, or Firm—Robert A. Elwell; Harold D. Jastram

[57] ABSTRACT

An external anchoring system for securing medical tubing to a body includes a resilient receptor disposed upon the exterior of a tube to be anchored; means for attachment of the anchoring system to the body; means for linking connected to the means for attachment to the body; and a knoblet projecting from the means for linking. The resilient receptor provides a reversible interference fit for the knoblet. Preferably, the resilient receptor is one of a plurality of resilient receptors disposed longitudinally on the tubing. Also, a method for anchoring a non-inserted portion of a naso-gastric catheter to the nose of a patient is disclosed and includes the steps of providing a naso-gastric catheter having a resilient receptor; providing a link having a nose attachment on one end and a knoblet on the opposite end; attaching the link to the nose; and inserting the knoblet into the resilient receptor.

9 Claims, 1 Drawing Sheet

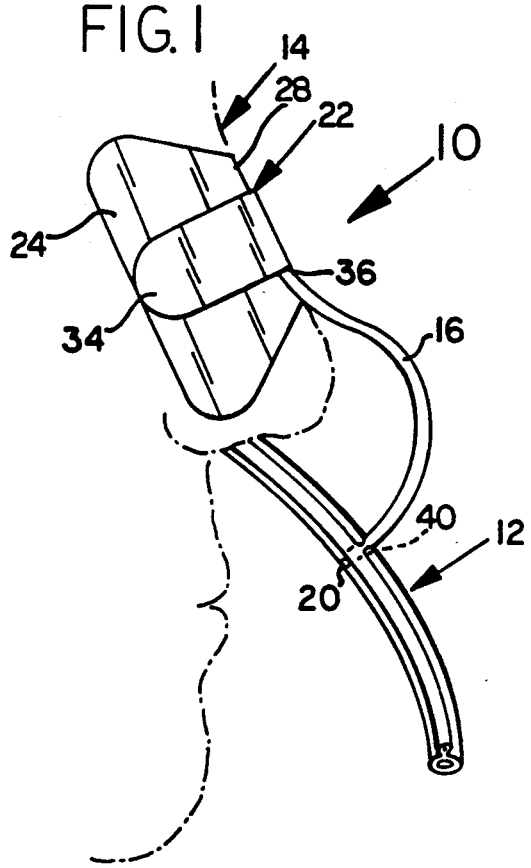
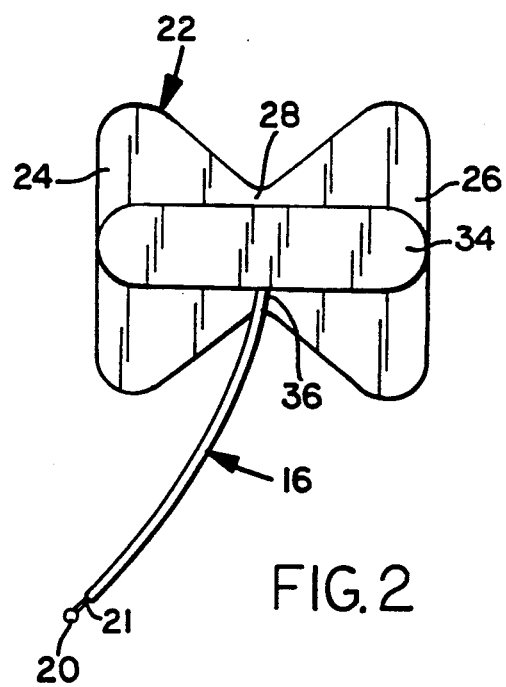
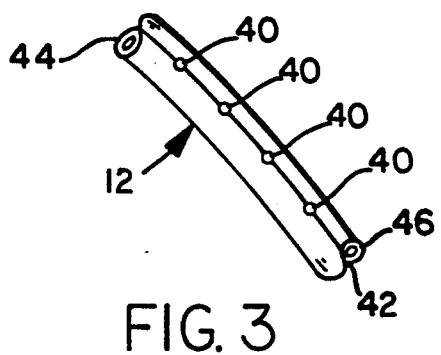

NASO-GASTRIC CATHETER ANCHOR SYSTEM

BACKGROUND OF THE INVENTION

The present invention pertains generally to medical and surgical tube holding devices, and more particularly to devices for anchoring a tube, such as a catheter, in position relative to a patient's body.

Many medical or surgical treatments necessitate the provision of an unobstructed passageway into a patient's body. Typically, such a passageway is provided by installing one or more tubes into the body. In some situations, the tube or tubes passes through the skin of the patient. In other situations, the tube enters the patient's body at a natural orifice. In both situations, the problem of anchoring or holding the tube to the patient's body must be addressed. Two general approaches are known: internal anchor systems and external anchor systems. By anchor system herein is meant at least two attachments, an attachment to a patient and an attachment to the tube. Additionally, anchor systems may involve a link between the two attachments.

U.S. Pat. No. Pat. No. 4,156,428 shows an example of an internal anchor system: specifically, an expansive cuff on the tube is inflated to create an anchor region within a patient's trachea.

With respect to external anchor systems, several variations are known. In one approach, the tube is directly secured to the patient by suturing the tube to the body, as shown in the H'Doubler, U.S. Pat. No. 3,176,690, or the Sheridan, U.S. Pat. No. 3,777,690, patents. Although suturing provides a secure attachment with respect to both the patient's body and the tube, it is difficult to interchange or readjust the tube. In the particular case of naso-gastric catheter, suturing the tube to the patient's face or nose is particularly objectionable.

One alternative to a suture attachment to the patient involves mechanical encircling of a portion of the patient's body. The Roxburg patent U.S. Pat. No. 4,527,559 discloses an anchoring of an endotracheal tube by the use of twill tape tied about a patient's neck. Anchoring systems which avoid suture attachments to the patient also generally employ an alternative attachment to the tube. The Roxburg endotracheal tube includes transverse apertures through which the twill tape is threaded to provide a secure attachment to the tube.

The Foster, U.S. Pat. No. 4,331,143, Carroll, U.S. Pat. No. 4,844,061 and Smith U.S. Pat. No. 4,592,351 patents show patient attachments involving encircling the patient's head with straps. In these three patents, adhesive attachments are used to secure the tube in the anchor system.

The attachment to the patient can also entail an adhesive attachment. Examples of adhesive attachments to patients in regards to anchoring a tube are shown in Lund U.S. Pat. No. 3,288,136, Kraviec U.S. Pat. No. 3,146,778, Kalt U.S. Pat. No. 4,838,878, Beisang U.S. Pat. No. 4,823,789, Page U.S. Pat. No. 3,782,388, Coleman U.S. Pat. No. 3,977,407, Taylor U.S. Pat. No. 4,057,066, and Moor U.S. Pat. No. 4,120,304. Initial adhesive attachments to a patient are typically satisfactory. However, if the adhesive attachment to the patient's skin must be repeatedly removed and replaced, the patient's skin can become very sore and irritated.

Many anchoring systems employing adhesive attachments to a patient include some separation of the attachments to the tube and to the patient. Separation or linking of the attachment point to the tube from the patient is shown in the Foster, Smith, Coleman, and Moor patents. Flexibility in such separation or linking is shown in Page. Flexible links, in the case of naso-gastric catheters, provide a greater level of patient comfort. The Krawiec patent shows a snap attachment system located roughly midway in a flexible link. The snap also contributes some of the flexibility in the Krawiec system. When unsnapped, a portion of the tether adhesively attached to the catheter continues to project from the tube, thus preventing the possibility of further insertion into the patient and also incurring the danger of snagging.

Adhesive attachments to the tube may be a problem after the tube has been in place some time. The adhesive attachment may be weakened by secretions and bodily fluids from the patient. Further, if the tube is to be readjusted relative to the original anchor point, the establishment of a new attachment to the tube may be particularly difficult since the patient's secretions and fluids tend to coat the tube and inhibit formation of new adhesive attachments.

Prior art tube attachments which are alternatives to adhesive include clamp mechanisms such as disclosed in the Lund, Moor, and Page patents. Such alternative attachments are generally objectionable in their tendency to at least partially deform the tube and thereby restrict or reduce the bore of the tube when clamped sufficiently tightly upon the tube to fully prevent any lengthwise tube movement.

Thus there exists a need for a tube anchoring system which allows for the establishment of an initial, semipermanent, attachment to an external portion of a patient's body and a simple, yet dependable, attachment to a tube. Such a system ideally should incorporate a mechanism for either adjusting or exchanging tubes without disturbing the initial attachment to the patient's body.

SUMMARY OF THE INVENTION

Naso-gastric tubes or catheters are commonly used in health care to empty a patient's stomach. The tube is passed through the patient's nose, thence through the esophagus, to the stomach. Subsequently, the catheter is stabalized by anchoring to the patient's nose. Frequently, the initial anchoring proves inappropriate and requires replacement. The present invention is particularly applicable for the anchoring of a naso-gastric catheter to a patient's nose.

The present invention includes an external anchoring system for securing medical tubing to a body. The anchoring system includes: means for attachment of the anchoring system to the body; means for linking connected to the means for attachment to the body; and means for reversible attachment of the tube. Preferably the means for reversible attachment of the tube includes a knoblet projecting from the means for linking and a resilient receptor on the tube capable of providing a reversible interference fit for the knoblet. Most preferably, the resilient receptor is one of a plurality of resilient receptors disposed longitudinally on the tube.

Additionally, the present invention includes a method for anchoring a non-inserted portion of a naso-gastric catheter to the nose of a patient. The method includes the steps of: providing a catheter having a resilient receptor; providing a flexible link having nose attachment on one end and a knoblet on the opposite end;

attaching the flexible link to the nose; and inserting the knoblet of the flexible link into the resilient receptor on the tube. Preferably, the method of this invention allows for selection of a desirably situated resilient receptor from amongst a plurality of longitudinally disposed resilient receptors on the tube.

BRIEF DESCRIPTION OF THE DRAWINGS

FIG. 1 is a side-view of a preferred embodiment of the anchoring system of the present invention, with a portion of the patient shown in phantom;

FIG. 2 is a top-view of an adhesive tape, link and knoblet; and

FIG. 3 is a top-view of a portion of a naso-gastric tube having resilient receptors.

DETAILED DESCRIPTION OF THE PREFERRED EMBODIMENTS

A preferred embodiment of the present invention is an external anchoring system 10, as shown in FIG. 1, for securing a naso-gastric catheter or tube 12 to a patient's nose 14. The anchor system 10 may be viewed as including an attachment for the body, a reversible attachment for the tube 12, and a link 16 joining the two attachments. The reversible tube attachment of the anchoring system 10 includes a resilient receptor 40 on the exterior of the naso-gastric tube 12 and a knoblet 20 projecting from the flexible link 16. The resilient receptor 40 provides an interference fit or reversible mating arrangement for the knoblet 20. The combination of the resilient receptor 40 and the knoblet 20, therefore, provide a reversible attachment of the tube 12 in the anchoring system 10. The link 16 is also connected to an adhesive tape 22. The adhesive tape 22 provides the attachment to the patient's body by adhering to the patient's nose 14. These components are further described and explained below.

The adhesive tape or nose piece 22, as shown in FIG. 2, preferably has a bilaterally symmetrical "butterfly" outline defined by left wing portion 24, a right wing portion 26, and a centrally located body portion 28 joining the two wings 24 and 26. The tape 22 may be a single sided medical grade adhesive tape.

A reinforcing band 34 connects an end 36 of the tether or flexible link 16 to the central body portion 28 of the butterfly shaped adhesive tape 22. Preferably, the reinforcing band 34 extends from adjacent the extreme edge of the left wing portion 24 to the extreme edge of the right wing portion 26, crossing the central body portion 28. The reinforcing band 34 is preferably formed of adhesive tape applied such that the adhesive side of the reinforcing band adheres to the nonadhesive side or back of the butterfly shaped adhesive tape 22.

The end portion 36 of the link 16 is firmly trapped between the back of the butterfly shaped adhesive tape 22 and the reinforcing band 34. Preferably, the link is attached such that it is directed away from the adhesive tape 22 generally along a line of symmetry running through the central body portion 28, as shown in FIG. 2. The tether or flexible link 16 may be a short length of small bore tubing. Alternatively the tether or flexible link 16 may be formed from a solid filament or braided material. The important properties of the tether or flexible link 16 are that it has a relatively constant length and that it has a relative amount of flexibility.

Other methods which strongly bond or connect the end 36 of the tether 16 to the tape 22 are also envisioned. Such methods include application of bonding glues.

Further embodiments are envisioned which employ integral extensions of the adhesive tape 22 to serve as a tether or link 16. In the embodiment employing an integral extension of the tape 22 to form a link 16, the portion of tape forming the link 16 preferably is rendered non-adhesive either by inclusion of a backing sheet to cover the adhesive or by folding the adhesive side of the tape against itself.

Extending from the opposite or free end of the link 16 is a knoblet 20. The knoblet 20 is preferably a small spherical member on a shank 21 of smaller radius than the spherical member. The knoblet 20 and shank 21 may be either a separate portion permanently fastened to the link 16 or may be an integral formation extending from the link 16. In the embodiment employing small diameter tubing as the link 16, a common pin may be employed, with the head of the pin serving as the knoblet 20 and the shank of the pin inserted into the free end of the link 16. If the shank 21 of the pin includes a barb (not shown), then insertion of such a pin into the bore of the small diameter tubing serving as the link 16 easily provides a satisfactory affixed knoblet 20.

The adhesive tape 22 is adapted to firmly attach to a patient's nose 14, as shown in FIG. 1, with central body portion 28 adhering to the ridge of the nose 14 and the left wing portion 24 adhering to the right side of the patient's nose 14 and the right wing adhering to the left side of the nose (not shown). This arrangement of the adhesive tape 22 upon the nose 14 results in the link 16 extending generally downward past the of the nose 14 (rather than upward which potentially could interfering with the patient's vision.)

The naso-gastric tube 12 includes a plurality of resilient receptors 40 longitudinally disposed along the exterior of the tube 12. The resilient receptors 40 are capable of providing a reversible interference fit for the knoblet 20. Because the knoblet 20 is on a shank 21 of smaller radius than the knoblet 20, insertion of the knoblet 20 into the resilient receptor 40 provides a dependable yet reversible attachment of the tube 12 to the anchor system. The knoblet 20 may be subsequently withdrawn from the resilient receptor 40 to facilitate selection of an alternatively situated resilient receptor 40.

Preferably the plurality of resilient receptors 40 extend over a length of about 30 cm each direction, (proximal and distal) of the typical point where a prior art naso-gastric tube would be taped to a patient's nose 14. This allows readjustment of the attachment to the tube 12 without removal and replacement of the tape portion 22 upon the patient's nose 14. Further, since the resilient receptors 40 do not require any interfering projections from the relatively smooth profile of the tube 12, portions of the tube 12 bearing resilient receptors 40 may be and typically are inserted in the patient during intubation.

Preferably, the resilient receptors 40 are provided by employing a double lumen type naso-gastric tube 12. The bond 42 between the first lumen 44 and the second lumen 46 is broken by inserting an object such as an ice pick, knife, or screw driver blade between the exterior walls of the first 44 and second 46 lumens. By repeating the insertion and separating the bond at spaced apart intervals along the tube, a plurality of resilient receptors are provided. The resilient property is contributed by the lumens. Most preferably, the second lumen 46 is a tube with a relatively smaller diameter and relatively thinner walls than the first lumen. In such an arrangement, the second tube 46 is more resiliently yieldable than the first tube 44 and, therefore, provides the resiliency to the receptor 40, while maintaining the first lumen 44 in a substantially undeformed condition during insertion or withdrawal of the knoblet 20. In contrast to prior art clamping arrangements as disclosed in the U.S. Pat. Nos. 3,288,136 and 3,782,388, this embodiment of the present invention prevents lengthwise movement of the naso-gastric tube 12 without restricting the first lumen 44.

The attachment of the tube 12 provided by the knoblet 20 and resilient receptors 40 of the present invention is also more dependable than the prior art method of attachment involving attempted creation of an adhesive bond between the naso-gastric tube 12 and adhesive tape. Specifically, the knoblet 20 and resilient receptors 40 are substantially unaffected by nasal secretions which tend to interfere with the prior art adhesive bonds, particularly during reapplications. The present invention also includes a method of anchoring a naso-gastric catheter to the nose of a patient. The method includes three steps: providing a catheter having a resilient receptor; providing a flexible link having a nose attachment on one end and a knoblet on the opposite end; attaching the link to the patient's nose; and inserting the knoblet in the resilient receptor to attach the tube and complete the anchoring of the naso-gastric tube to the patient's nose. Typically, such a method would be performed in conjunction with intubation of a naso-gastric catheter and the resilient receptor located on the catheter at a desirable distance from the inserted end of the catheter. In a preferred embodiment of the method of the present invention, the catheter includes a plurality of resilient receptors longitudinally disposed along the catheter. In such an embodiment, the method includes selection of a desirably situated receptor from amongst the plurality of receptors. In a most preferred embodiment, the method further includes withdrawal of the knoblet from the initially selected receptor, readjustment of the extent of catheter insertion and insertion of the knoblet in a newly selected receptor.

In conclusion, the attachment system of the present invention provides an efficient device and method of adjusting the positioning of a naso-gastric tube anchor point adjacent a patient's nose. The anchor attachment may be adjusted without removal and replacement of an initially applied adhesive tape attachment on a patient's nose. Further, the elimination of the need for formation of an adhesive bond to the naso-gastric tube by the knoblet and resilient receptor improves the dependability of the attachment by circumventing the problems normally associated with nasal secretions and avoiding clamps which deform the bore of the tube. Finally, the attachment system of the present invention through the provision of these advantages, encourages fine adjustment of a naso gastric tube since the readjustment problems associated with the prior art are avoided.

It will be readily recognized by workers skilled in the art that with minor variations in the attachment herein disclosed for the patient's nose, the anchor system may be adapted for wide range of anchoring applications throughout the medical and veterinary arts, in situations requiring easily attached and reversible anchoring systems.

Although the present invention has been described with reference to the preferred embodiments, workers skilled in the art will recognize that changes may be made in form and detail without departing from the spirit and scope of the invention.

What is claimed is:

1. An external anchoring system for securing naso-gastric tubing to a patient's nose, the system comprising:
    means for adhesive attachment to the patient's nose;
    nasogastric tubing including a first tube and a second tube longitudinally intermittently joined to the first tube to define at least one resilient receptor situated between the first tube and the second tube, said second tube being more resiliently yieldable than said first tube;
    means for reversible linking of the naso-gastric tubing to the means for adhesive attachment including a tether attachment having a main portion secured at a first end to the means for adhesive attachment and at a second end having a reduced diameter shank portion ending in a knoblet;
    means for removably inserting said knoblet in said receptor in an interference fit to secure the nasogastric tubing to the patient's nose, said means for removably inserting said knoblet comprising receipt of said knoblet through said receptor, and said reduced diameter shank portion being received within said receptor, whereby said knoblet and said main portion of said tether abut opposite sides of said receptor with said shank portion received within said receptor.

2. The anchoring system of claim 1 and wherein the receptor is one of a plurality of resilient receptors longitudinally spaced apart along the tubing between said first and said second tube.

3. The anchoring system of claim 1 wherein the tubing comprises a first tube and a second tube external and parallel to the first tube, bonded together in at least two longitudinally spaced apart segments and wherein the resilient receptor is defined by the adjoining external walls of the unbonded segment between the two longitudinally spaced apart bonded segments.

4. The anchoring system of claim 3 wherein the resilient receptor is one of a plurality of resilient receptors longitudinally disposed along the tubing.

5. The anchoring system of claim 1 wherein the means for attachment to the body comprises a medical grade adhesive.

6. The anchoring system of claim 5 wherein the means for attachment to the body comprises a butterfly shaped adhesive tape adapted for application to a patient's nose.

7. The anchoring system of claim 1 wherein the means for linking is flexible.

8. A method for anchoring a non-inserted portion of a naso-gastric catheter to the nose of a patient comprising the steps:
    providing a catheter having a first tube and a second more resilient tube longitudinally intermittently joined to the first tube to define at least one resilient receptor situated between the first tube and the second tube;
    providing an adhesive attachment for application to the patient's nose;
    providing a tether having a main portion, a reduced diameter shank portion, and a knoblet;
    connecting said tether main portion to said adhesive attachment;
    inserting said knoblet through said resilient receptor; and leaving said shank portion within said resilient receptor, whereby said knoblet and said tether main portion abut said resilient receptor on opposite sides with said shank disposed within the receptor.

9. The method of claim 8 further including the steps of providing a plurality of longitudinally disposed resilient receptors on the catheter and selecting a desirably located resilient receptor prior to inserting said knoblet and said shank portion into said receptor.

* * * * *